United States Patent
Kawashima

(10) Patent No.: US 8,153,418 B2
(45) Date of Patent: Apr. 10, 2012

(54) APPARATUS AND METHOD FOR ANALYZING BACTERIA

(75) Inventor: Yasuyuki Kawashima, Kobe (JP)

(73) Assignee: Sysmex Corporation, Kobe (JP)

( * ) Notice: Subject to any disclaimer, the term of this patent is extended or adjusted under 35 U.S.C. 154(b) by 0 days.

(21) Appl. No.: 12/822,701

(22) Filed: Jun. 24, 2010

(65) Prior Publication Data

US 2010/0261225 A1    Oct. 14, 2010

Related U.S. Application Data

(63) Continuation of application No. 10/961,734, filed on Oct. 8, 2004, now abandoned.

(30) Foreign Application Priority Data

Oct. 10, 2003    (JP) ................................. 2003-352170

(51) Int. Cl.
*C12M 1/34* (2006.01)
*C12M 3/00* (2006.01)

(52) U.S. Cl. ............... 435/288.7; 435/288.3; 435/288.4; 435/288.5; 435/808; 378/44; 378/86; 378/70; 356/73; 356/301; 356/336; 356/335; 250/483.1; 250/574; 702/21

(58) Field of Classification Search ............... 435/288.7, 435/288.3, 288.4, 288.5, 808; 702/21; 378/44; 378/86, 70; 356/73, 301, 336, 335; 250/483.1, 250/574
See application file for complete search history.

(56) References Cited

U.S. PATENT DOCUMENTS

| | | | |
|---|---|---|---|
| 5,137,810 A | 8/1992 | Sizemore et al. | |
| 5,308,772 A | 5/1994 | Sakata et al. | |
| 5,545,535 A | 8/1996 | Roth et al. | |
| 6,662,117 B2 | 12/2003 | Naito | |
| 6,787,302 B2 | 9/2004 | Fleming et al. | |
| 2002/0006631 A1 | 1/2002 | Houwen et al. | |

OTHER PUBLICATIONS

Wakisaka et al., "A selective isolation procedure for Micromonospora," J. Antibiotics, vol. 25, pp. 822-836, 1982.

*Primary Examiner* — Nathan Bowers
(74) *Attorney, Agent, or Firm* — Brinks Hofer Gilson & Lione

(57) ABSTRACT

An apparatus for analyzing bacteria is described that includes an analytic sample preparation section for preparing an analytic sample by treating a specimen so as to generate a morphological difference between Gram-negative bacteria and Gram-positive bacteria, a detector for detecting optical information from each particle contained in the analytic sample and an analyzing section for detecting Gram-positive bacteria contained on the basis of the detected optical information. A method for analyzing bacteria is also described.

15 Claims, 11 Drawing Sheets

(Measurement A)

(Measurement B)

(Measurement A)

(Measurement B)

(Measurement A)

(Measurement B)

(Measurement A)

(Measurement B)

(Measurement A)

(Measurement B)

(Measurement A)

(Measurement B)

APPARATUS AND METHOD FOR ANALYZING BACTERIA

RELATED APPLICATIONS

This application is a continuation application of U.S. application Ser. No. 10/961,734 filed Oct. 8, 2004, now abandoned which claims priority under 35 U.S.C. §119 to Japanese Patent Application No. 2003-352170 filed Oct. 10, 2003, the entire content of which is hereby incorporated by reference.

BACKGROUND

1. Field of the Invention

The present invention relates to an apparatus and a method for detecting bacteria in a specimen and in particular to an apparatus and a method for detecting Gram-negative or Gram-positive bacteria contained in a specimen. The present invention also relates to an apparatus and a method for detecting Gram-negative and Gram-positive bacteria contained in a specimen.

2. Description of the Related Art

For generally classifying bacteria, the bacteria are first divided roughly into two groups of bacteria i.e. Gram-positive bacteria and Gram-negative bacteria, on the basis of Gram stainability. The classification by Gram stainability is the most fundamental standard for classifying bacteria, and Gram staining classification methods generally used at present include Gram staining methods such as a Hucker modified method and a Bartholomew & Mittwer method (Barmi method). These methods fundamentally require techniques wherein Gram stainability is judged by observing a stained specimen under a microscope.

As techniques of detecting and counting Gram-positive bacteria by using a flow cytometer, on one hand, a method described in U.S. Pat. No. 5,137,810 is known. In this method, lectin is used. The lectin is a sugar-binding protein, and sugar chains to which lectin binds exist on the cell surface of a bacterium. One kind of lectin, wheat germ agglutinin (WGA), has such properties as to bind to sugar chains existing abundantly on the cell surface of Gram-positive bacterium. Accordingly, Gram-positive bacteria can be detected by mixing fluorescence-labeled WGA with bacteria and detecting fluorescence.

As techniques of judging whether bacteria contained in a specimen are Gram-negative or Gram-positive bacteria and counting the bacteria by using a flow cytometer, a method described in U.S. Pat. No. 5,545,535 is known. This is a method of classifying Gram-negative and Gram-positive bacteria by staining bacteria with a reagent containing a plurality of fluorescent dyes different from one another in respect of staining specificity and fluorescence wavelength, and classifying the bacteria from the fluorescence pattern. For example, when SYTO 9 that is a fluorescent dye staining bacteria and hexidium iodide that is a fluorescent dye staining only Gram-positive bacteria are used, it can be judged that bacteria stained with both the dye are Gram-positive bacteria, while bacteria stained with only SYTO 9 are Gram-negative bacteria.

By the method using lectin described in U.S. Pat. No. 5,137,810, however, there are cases where accurate judgment results cannot be obtained depending on the kind of bacterium.

By the method using a plurality of fluorescent dyes described in U.S. Pat. No. 5,545,535, there are cases where accurate judgment results cannot be obtained because contaminants other than bacteria contained in a specimen are also stained.

BRIEF SUMMARY

The present invention provides an apparatus and a method for detecting Gram-negative or Gram-positive bacteria more easily, rapidly and accurately than the conventional techniques. Further, the present invention provides an apparatus and a method for detecting Gram-negative and Gram-positive bacteria more easily, rapidly and accurately than the conventional techniques.

DETAILED DESCRIPTION OF THE DRAWINGS AND THE PRESENTLY PREFERRED EMBODIMENTS

Hereinafter, the bacteria analyzing apparatus in one embodiment of the invention is described in detail by reference to the accompanying drawings. In this bacteria analyzing apparatus, an analytic sample to which an alkaline solution is not added and an analytic sample to which an alkaline solution is added are prepared, and bacteria in each sample are detected and counted.

Figure 1:
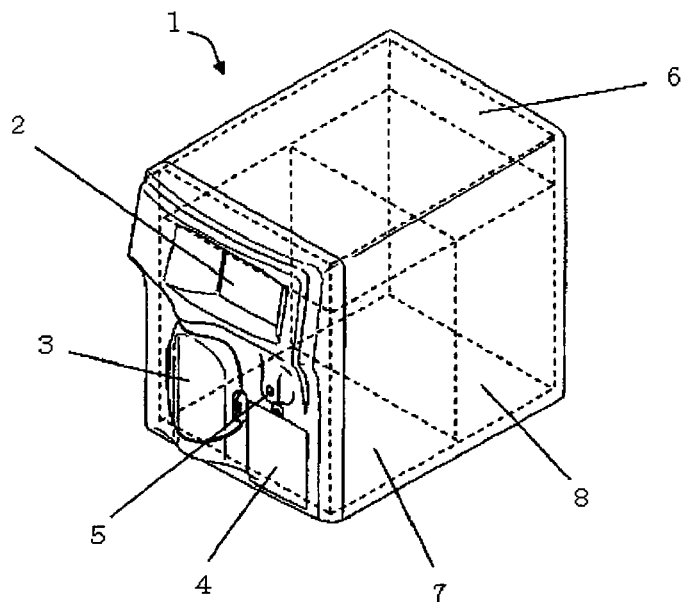
FIG. 1 shows the constitution of a bacteria analyzing apparatus in one embodiment of the present invention.

In FIG. 1, the outer appearance of bacteria analyzing apparatus 1 is shown by the solid line, and the constitution of the inside of the bacteria analyzing apparatus is shown by the broken line. On the outermost front of the bacteria analyzing apparatus 1, a liquid crystalline touch panel 2 for inputting settings and for displaying and outputting measurement results, a specimen setting section cover 3, a reagent setting section cover 4 and a start switch 5 are disposed. A control section 6 for controlling the movement of the bacteria analyzing apparatus and analytical processing is disposed in the upper space of the bacteria analyzing apparatus 1 shown by the broken line. In the front side of the lower space, an analytic sample preparation section 7 for preparing an analytic sample is disposed. In the rear side of the lower space, a measurement section 8 for detecting a signal from the analytic sample is disposed.

Figure 2:
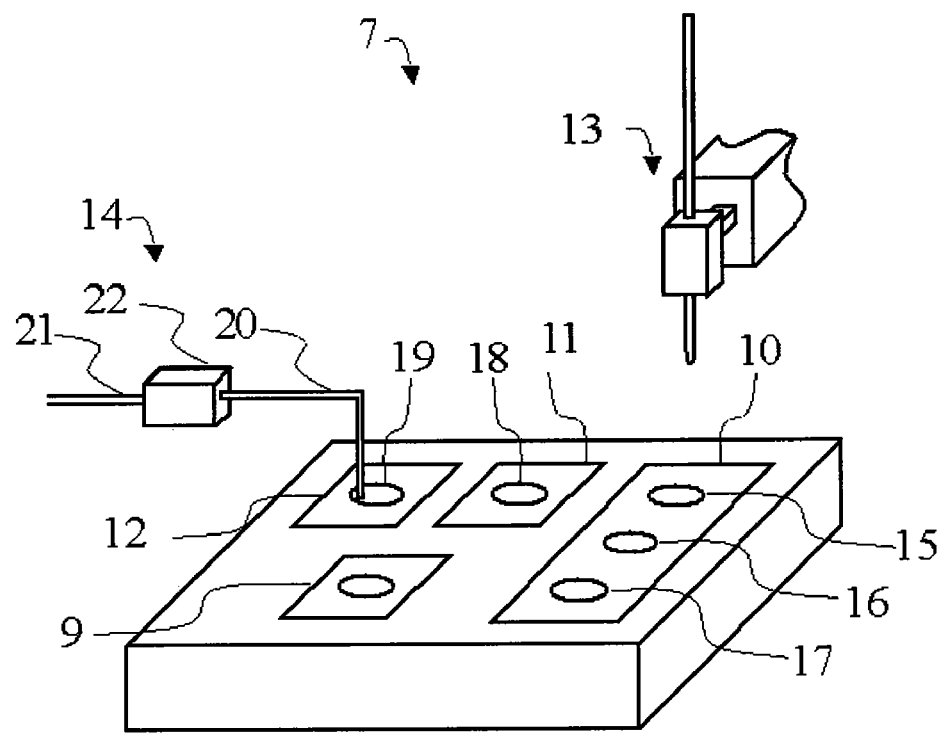
FIG. 2 shows an analytic sample preparation section in the bacteria analyzing apparatus in one embodiment of the present invention.

FIG. 2 shows the analytic sample preparation section 7. The analytic sample preparation section 7 includes a specimen setting section 9, a reagent setting section 10, a treatment section 11, a dyeing section 12, a pipetting device 13 and a liquid sending device 14. The operator opens the specimen setting section cover 3 in FIG. 1, and sets a specimen-containing sample container in the specimen setting section 9. The operator opens the reagent setting section cover 4 in FIG. 1, and sets an alkaline solution-containing micro test tube 15, a dye-containing micro test tube 16 and a diluent-containing micro test tube 17 respectively in the reagent setting section 10. In the treatment section 11, a micro test tube 18 is set, and the specimen is mixed with the alkaline solution whereby bacteria in the specimen are alkali-treated. Although not shown in the figure, the treatment section 11 is provided with a temperature-regulating mechanism for keeping the solution in the micro test tube 18 at a predetermined temperature and with a stirring mechanism for stirring the solution in the micro test tube 18. A micro test tube 19 is set in the dyeing section 12 where a dyeing solution and a diluent are mixed with the specimen or the mixture prepared in the treatment section 11, to prepare the analytic sample. Although not shown in the figure, the dyeing section 12 is provided with a temperature-regulating mechanism for keeping the solution in the micro test tube 19 at a predetermined temperature and with a stirring mechanism for stirring the solution in the micro test tube 19. A predetermined amount of liquid is suctioned or discharged through the top of the pipetting device 13, and the pipetting device 13 can move vertically and horizontally by a driving device not shown in the figure. The liquid sending device 14 includes a suction tube 20 for suctioning the analytic sample, a liquid sending tube 21 for transporting the analytic sample suctioned through the suction tube 20 to the measurement section 8 shown in FIG. 3, and a pump 22 for suctioning the analytic sample and sending the analytic sample to the measurement section 8. The suction tube 20 is inserted into the micro test tube 19 set in the dyeing section 12, in order to suction a predetermined amount of the analytic sample. The suctioned analytic sample is sent via the liquid sending tube 21 to the measurement section 8.

Figure 3:
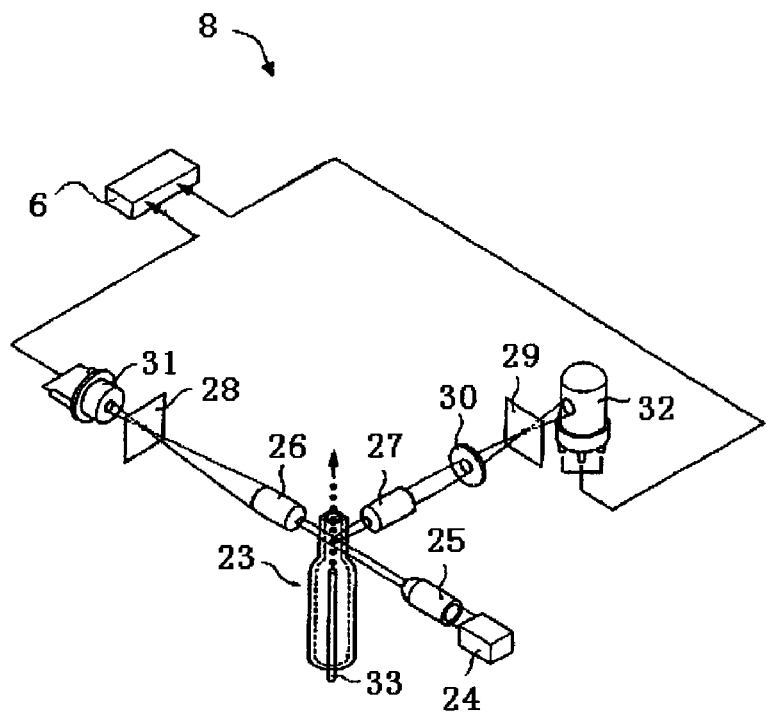
FIG. 3 shows a measurement section in the bacteria analyzing apparatus in one embodiment of the present invention.
Figure 4:
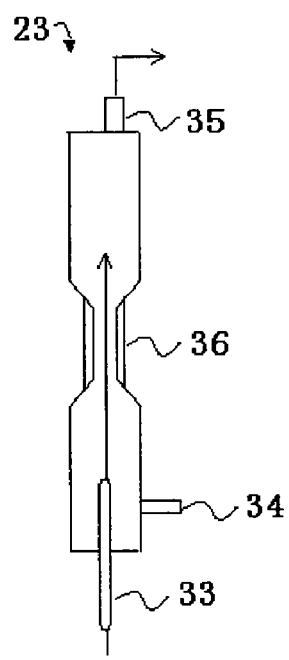
FIG. 4 shows a sheath flow cell part in the bacteria analyzing apparatus in one embodiment of the present invention.

FIG. 3 shows the measurement section 8. The measurement section 8 includes a sheath flow cell 23, a laser light source 24, a condenser lens 25, converging lenses 26 and 27, pinholes 28 and 29, a filter 30, a photodiode 31 and a photo-multiplier tube 32. The analytic sample prepared in the analytic sample preparation section 7 in FIG. 2 is passed through the sheath flow cell 23. The sheath flow cell 23 shown in FIG. 4 is provided with a sample nozzle 33 for upward jetting the analytic sample towards a narrow through-hole section 36, a sheath liquid supplying inlet 34, and an exhaust liquid outlet 35. The converging lenses 26 and 27 collect optical information such as forward scattered light and side fluorescence obtained from each particle in the analytic sample that has received a laser light. The photodiode 31 receives the forward scattered light, converts the light into electricity and outputs it as light signal. The photo-multiplier tube 32 receives the side fluorescence, converts the fluorescence into electricity and outputs it as light signal. Each outputted signal is sent to the control section 6.

Figure 5:
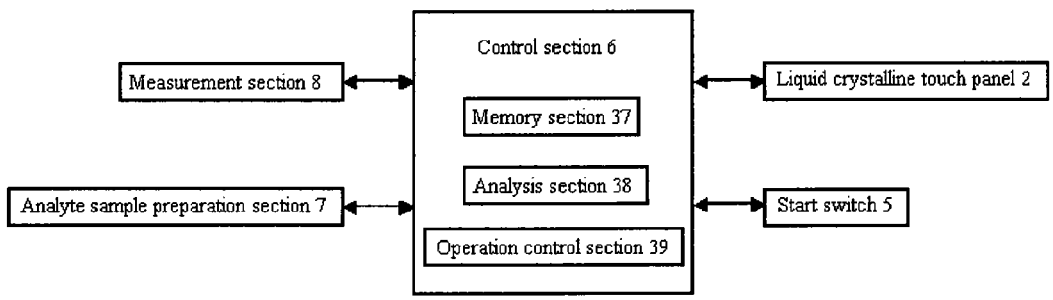
FIG. 5 shows the relationship between a control section and each unit in the bacteria analyzing apparatus in one embodiment of the present invention.

FIG. 5 shows the constitution of the control section 6 and the relationship between the control section 6 and each section of the apparatus. The control section 6 has a microcomputer having a central processing unit (CPU) and memory devices such as ROM/RAM and circuits for processing signals sent from the measurement section 8. The control section 6 plays a role as memory section 37, analysis section 38 and operational control section 39. The memory section 37 memorizes an analysis program for analyzing signals obtained from particles in the analytic sample and a control program for controlling the operations of each section in the apparatus. Data on signals detected in the measurement section 8, and processing results by the analysis program, are also memorized in the memory section 37. In the analysis section 38, a signal detected in the measurement section 8 is analyzed on the basis of the analysis program, to form data on bacteria contained in the analytic sample. The data formed in the analysis section 38 are output to the liquid crystalline touch panel 2. The operational control section 39 controls the operations of each section in the apparatus, on the basis of the control program memorized in the memory section 37.

Hereinafter, the operations of each section are described in more detail.

First, the operator sets a specimen and a measurement reagent in predetermined positions in the analytic sample preparation section 7. By opening the specimen setting section cover 3 in FIG. 1, the specimen can be set in the specimen setting section 9 in the analytic sample preparation section 7 in FIG. 2. By opening the reagent setting section cover 4, reagents such as an alkaline solution, a dyeing solution and a diluent can be set in the reagent setting section 10 in the analytic sample preparation section 7, whereby the alkaline solution-containing micro test tube 15, the dye-containing micro test tube 16 and the diluent-containing micro test tube 17 can be set respectively.

A bacteria-containing liquid is used as the specimen. For example, a culture solution obtained by culturing bacteria in a medium, or a clinical sample such as bacteria-containing urine and blood, or the like can be used as the specimen.

The alkaline solution added in alkali treatment to the specimen is desirably an alkaline solution at about pH 14. For example, the alkaline solution includes a potassium hydroxide solution (KOH solution) and sodium hydroxide solution (NaOH solution). When the specimen is treated with the alkali, Gram-negative bacteria contained in the specimen are damaged and shrunk thus undergoing a morphological change. On the other hand, Gram-positive bacteria do not undergo a morphological change. This is because the surface layer of Gram-negative bacteria is thinner than the surface layer of Gram-positive bacteria, and thus the surface layer of Gram-negative bacteria is damaged more easily than the surface layer of Gram-positive bacteria. As a result, the particles of Gram-negative bacteria are made considerably smaller than those of Gram-positive bacteria, and the degree of staining of Gram-negative bacteria is lowered. In this example, the caused morphological difference between Gram-negative bacteria and Gram-positive bacteria is utilized to analyze Gram-negative bacteria and Gram-positive bacteria contained in the specimen.

The concentration of KOH solution is preferably 5 to 25%, most preferably 10 to 20%. In alkali treatment with the alkaline solution, the morphological change may hardly occur in some Gram-negative bacteria. As a method of solving this problem, a method of alkali treatment with an alkaline solution containing a surfactant was found by the present inventors. By alkali treatment with the alkaline solution containing a surfactant, the morphological change in Gram-negative bacteria can be stably caused. The usable surfactant includes an amphoteric surfactant and a nonionic surfactant. The amphoteric surfactant is not particularly limited, but preferably betaine- and amine oxide-based surfactants are mentioned. The nonionic surfactant is not particularly limited, but preferably alkyl phenol-based surfactants and Triton are mentioned. In this example, Triton is used. The concentration of Triton contained in KOH is preferably 0.01 to 0.05 g/ml, most preferably 0.02 to 0.04 g/ml. In this example, 10% KOH solution containing 0.02 g/ml Triton is used.

The dyeing solution used in this example is the one containing a polymethine-based fluorescent dye represented by the structural formula below. However, the dye contained in the dyeing solution is not particularly limited insofar as bacteria can be stained. From the viewpoint of the ability to detect bacteria, a fluorescent dye binding to at least one of the components constituting bacteria and emitting fluorescence is desirably used. The polymethine-based fluorescent dye used in this example has a property of binding specifically to nucleic acid of bacteria, and thus by a dyeing solution containing this dye, bacteria only can be specifically stained while contaminants are hardly stained.

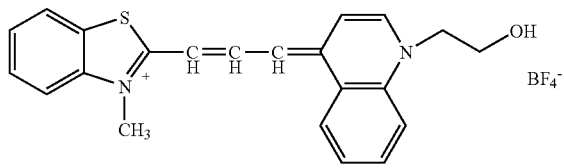

As the diluent, a surfactant-containing solution having a buffering action in the vicinity of pH 2.0 to 4.5 is used. In the case of using the dyeing solution containing the fluorescent dye, dyeing under acid conditions is desirable to suppress dyeing contaminants more effectively. In this example, the diluent was prepared at pH 2.5. The surfactant contained in the diluent includes a cationic surfactant, an anionic surfactant, an amphoteric surfactant and a nonionic surfactant. As the diluent in this example, a diluent having the following composition containing a cationic surfactant is used. In this example, tetradecyltrimethyl ammonium bromide was used as the cationic surfactant.

| Reagent composition (diluent) | |
|---|---|
| Citric acid | 100 mM |
| Sodium sulfate | 90 mM |
| Amide sulfuric acid | 100 mM |
| Tetradecyltrimethyl ammonium bromide | 0.1% |
| NaOH | added in an amount to adjust the diluent to pH 2.5 |

Figure 6:
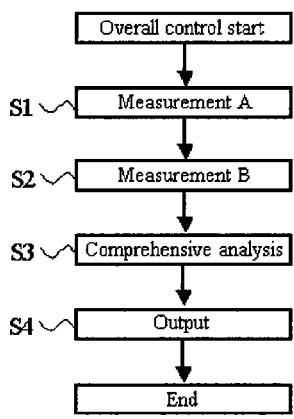
FIG. 6 shows the flow of overall control of the bacteria analyzing apparatus in one embodiment of the present invention.

As described above, a specimen and reagents are set, and the start switch 5 is pushed, whereby an overall control is started. FIG. 6 is a flow chart showing the flow of the overall control by the control program. When the start switch is pushed, S1 (measurement A), S2 (measurement B), S3 (comprehensive analysis) and S4 (output) are executed successively. The analytic sample preparation section 7, measurement section 8, and analysis section 38 are regulated by the control program, and a series of operations is automatically executed. The above-mentioned S1, S2, S3 and S4 are described in detail.

S1 (Measurement A)

Figure 7:
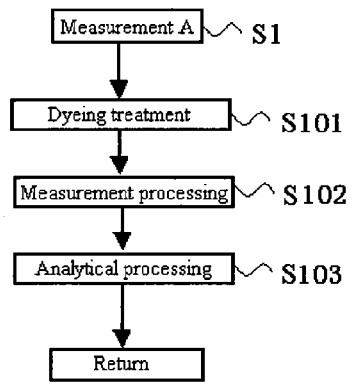
FIG. 7 shows the flow of measurement A in one embodiment of the present invention.

FIG. 7 is a flow chart of measurement A. In measurement A, a analytic sample is prepared without adding the alkaline solution to a specimen, and both Gram-negative and Gram-positive bacteria (referred to hereinafter, as total bacteria) contained in the sample are detected, and as shown in FIG. 7, measurement A is comprised of S101 (dyeing treatment), S102 (measurement processing) and S103 (analytical processing). The operations of each section in each step are described below. S101 (dyeing treatment) is the operation of the analytic sample preparation section 7.

S101 (Dyeing Treatment)

The operation of the analytic sample preparation section 7 in dyeing treatment is described by reference to FIG. 2. First, the pipetting device 13 suctions a specimen from a specimen container set in the specimen setting section 9, and 25 µl of the specimen is pipetted into the micro test tube 19 set in the dyeing section 12. Then, the pipetting device 13 suctions the diluent from a micro test tube 17 set in the reagent setting section 10, and 365 µl of the diluent is pipetted into the micro test tube 19 set in the dyeing section 12. Further, the pipetting device 13 suctions the dyeing solution from a micro test tube 16 set in the reagent setting section 10, and 10 µl of the dyeing solution is pipetted into the micro test tube 19 set in the dyeing section 12. Thereafter, the dyeing section 12 stirs the micro test tube 19 for 30 seconds while the temperature is kept at 42° C. An analytic sample is thereby prepared in the micro test tube 19. After the analytic sample is thus prepared, the analytic sample is suctioned by the liquid sending device 14 from the micro test tube 19 in the dyeing section 12 and sent to the sheath flow cell 23 in the measurement section 8.

S102 (Measurement Processing)

The operation of the measurement section 8 in measurement processing is described by reference to FIGS. 3 and 4. The analytic sample prepared in the analytic sample preparation section 7 is sent to the sheath flow cell 23 and discharged from the sample nozzle 33 to the sheath flow cell. Simultaneously, a sheath solution is discharged from the sheath liquid supplying inlet 34 into the sheath flow cell. The analytic sample is thereby surrounded by the sheath solution within the sheath flow cell, and flows as a thinner stream by the narrow through-hole section 36. The flowing solution is made as thin as the diameter of bacterial particle, and thus the particles contained in the analytic sample can flow in a line in the narrow through-hole section 36.

Laser light emitted from the laser light source 24 is condensed by the condenser lens 25 and applied onto the sample stream running through the narrow through-hole section 36. Forward scattered light emitted from each of the particles in the sample that has received the laser light is condensed by the converging lens 26 and passed through a pinhole 28. Side florescence is condensed by the converging lens 27 and passed through filter 30 and pinhole 29. The forward scattered light is received by photodiode 31, converted from light into electricity, and outputted as forward scattered light signal. The side fluorescence is received by photo multiplier tube 32, converted from light into electricity, and outputted as side fluorescence signal. Each outputted signal is sent to the control section 6 and memorized as data on each particle in the memory section 37.

S103 (Analytical Processing)

Figure 8:
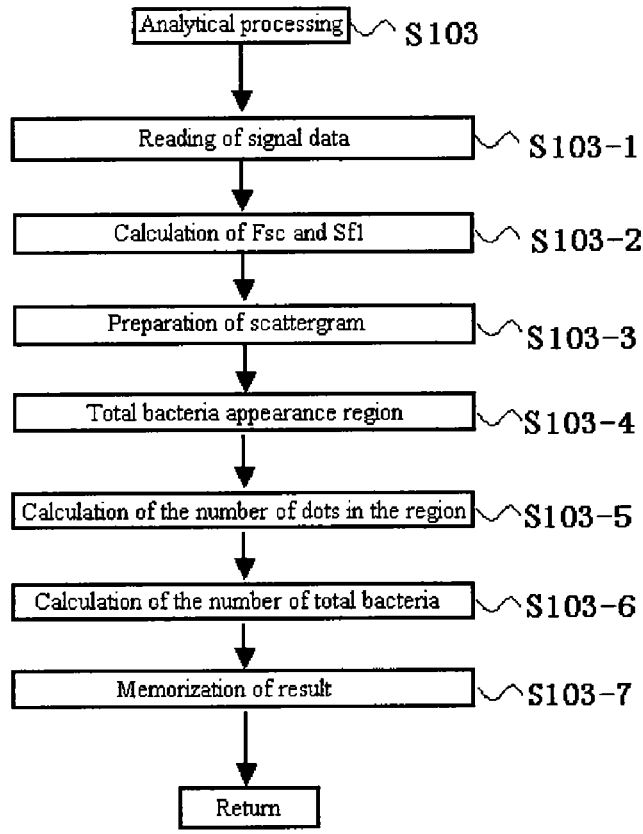
FIG. 8 shows the flow of analysis in measurement A in one embodiment of the present invention.

When the forward scattered light signal and side fluorescence signal are detected by measurement in S102, the analysis section 38 analyzes each signal, on the basis of an analysis program. The operation of the analysis program in analytical processing is described by reference to the flow chart in FIG. 8. Each step in the flow chart is as follows:

S103-1: Data on the forward scattered light signal and side fluorescence signal detected from the sample are read from the memory section 37. The procedure is followed by S103-2.

S103-2: On the basis of the forward scattered light signal and side fluorescence signal obtained from each particle in the analytic sample, the forward scattered light intensity (Fsc) and side fluorescence intensity (FL) are calculated. The procedure is followed by S103-3.

S103-3: Fsc and FL for each particle calculated in S103-2 are used as parameters to prepare a scattergram. First, two-dimensional coordinates with Fsc and FL coordinate axes are developed, and on the basis of Fsc and FL, a coordinate position corresponding to each particle in the analytic sample is determined. The scattergram with Fsc and FL as parameters is thus prepared. The procedure is followed by S103-4.

Figure 12A:
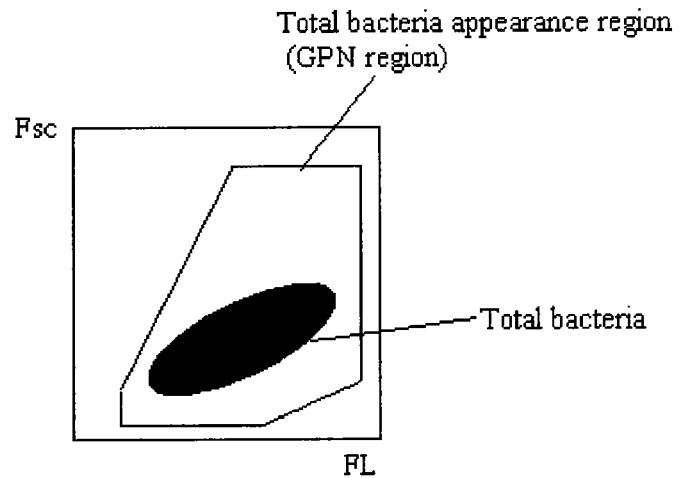
FIGS. 12A and 12B show one example of a two-dimensional scattergram prepared by the bacteria analyzing apparatus in one embodiment of the present invention.

S103-4: On the prepared scattergram, a region where total bacteria appear (this region is referred to as GPN region) is established. The GPN region is established on the scattergram, as shown in FIG. 12A. The GPN region thus established is empirically determined by previously measuring the analytic sample containing Gram-negative and Gram-positive bacteria. Both dots corresponding to Gram-negative bacteria and dots corresponding to Gram-positive bacteria, contained in the sample, appear in the GPN region. The GPN region is memorized in the memory section 37, read by the analysis program in S103-4, and applied to the scattergram. The procedure is followed by S103-5.

S103-5: The number of dots in the GPN region is counted. This is followed by S103-6.

S103-6: On the basis of the number of dots counted in S103-5, the number of total bacteria contained in the specimen is calculated. On the scattergram, dots corresponding to the total bacteria appear on the GPN region. On the basis of the number of dots appearing on the GPN region, the number of the total bacteria contained in the specimen can be calculated. In this example, the number of total bacteria contained per μL of the specimen is calculated from the determined number of dots. This is followed by S103-7.

S103-7: Data on the number of dots in the GPN region calculated in S103-5 and data on the number of total bacteria calculated in S103-6 are memorized.

As described above, FIG. 12A is shown to explain the scattergram prepared in S103-3 and S103-4. In the scattergram, FL is shown on the abscissa, and Fsc on the ordinate. The value of FL is increased in the direction from left to right on the abscissa. The value of Fsc is increased in the upward direction on the ordinate. Both Gram-negative bacteria and Gram-positive bacteria contained in the sample appear on the GPN region established on the scattergram.

S2 (Measurement B)

Figure 9:
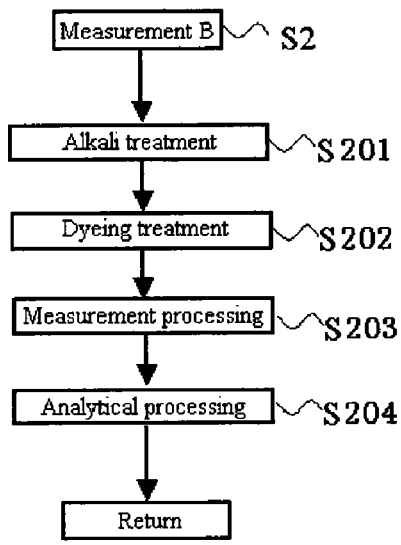
FIG. 9 shows the flow of measurement B in one embodiment of the present invention.

FIG. 9 is a flow chart of measurement B. In measurement B, the same specimen as used in measurement A is used. In measurement B, an alkaline solution (10% KOH solution containing a nonionic surfactant Triton) is added to the specimen, whereby a morphological change is caused in only Gram-negative bacteria in the specimen, and Gram-positive bacteria contained in the specimen are detected, and as shown in FIG. 9, measurement B is comprised of S201 (alkali treatment), S202 (dyeing treatment), S203 (measurement processing) and S204 (analytical processing). The operations of each section in the analyzer in each step are described below. S201 (alkali treatment) and S202 (dyeing treatment) are the operations of the analytic sample preparation section 7.

S201 (Alkali Treatment)

The operations of the analytic sample preparation section 7 in alkali treatment with an alkaline solution are described by reference to FIG. 2. First, the pipetting device 13 suctions a specimen from a specimen container set in the specimen setting section 9, and 25 μl of the specimen is pipetted into the micro test tube 18 set in the treatment section 11. Then, the pipetting device 13 suctions the alkaline solution from a micro test tube 15 set in the reagent setting section 10, and 25 μl of the alkaline solution is pipetted into the micro test tube 18 set in the treatment section 11. In the treatment section 11, the micro test tube 18 is kept at a temperature of 42° C. under stirring for 10 seconds. In this manner, 50 μl sample wherein the bacteria were alkali-treated is prepared in the micro test tube 18. After the alkali-treated sample is prepared, the pipetting device 13 suctions the sample and pipettes it the micro test tube 19 set in the dyeing section 12.

S202 (Dyeing Treatment)

The operations of the analytic sample preparation section 7 in dyeing treatment are described by reference to FIG. 2. When the sample is sent to the micro test tube 19 in the dyeing section 12 in the step of S201, the pipetting device 13 suctions the diluent from a micro test tube 17 set in the reagent setting section 10, and 340 μl of the diluent is pipetted in the micro test tube 19 set in the dyeing section 12. Further, the pipetting device 13 suctions the dyeing solution from a micro test tube 16 set in the reagent setting section 10, and 10 μL of the dyeing solution is pipetted in the micro test tube 19 set in the dyeing section 12. Thereafter, the micro test tube 19 is maintained at 42° C. under stirring for 30 seconds in the dyeing section 12. In this manner, the analytic sample to which the alkaline solution was added is prepared in the micro test tube 19.

In preparation of the analytic sample in measurement B described above, an alkaline solution is used to treat the specimen under alkaline conditions, and then bacteria contained in the specimen is stained. As a result, Gram-negative bacteria have underwent the morphological change, and thus their particles are very smaller than particles of Gram-positive bacteria, and the degree of staining of Gram-negative bacteria is significantly reduced. Accordingly, the Gram-negative bacteria and Gram-positive bacteria can be easily distinguished from each other by differences in the forward scattered light intensity and fluorescence intensity.

When the analytic sample is prepared in this manner, the liquid sending device 14 suctions the analytic sample from the micro test tube 19 in the dyeing section 12, and sends it to the sheath flow cell 23 in the measurement section 8.

S203 (Measurement Processing)

The measurement section 8 in measurement processing is actuated in the same manner as in S102 (measurement processing) in measurement A, and forward scattered light signal and side fluorescence signal are detected, and each detected signal is sent to the memory section 37.

S204 (Analytical Processing)

Figure 10:
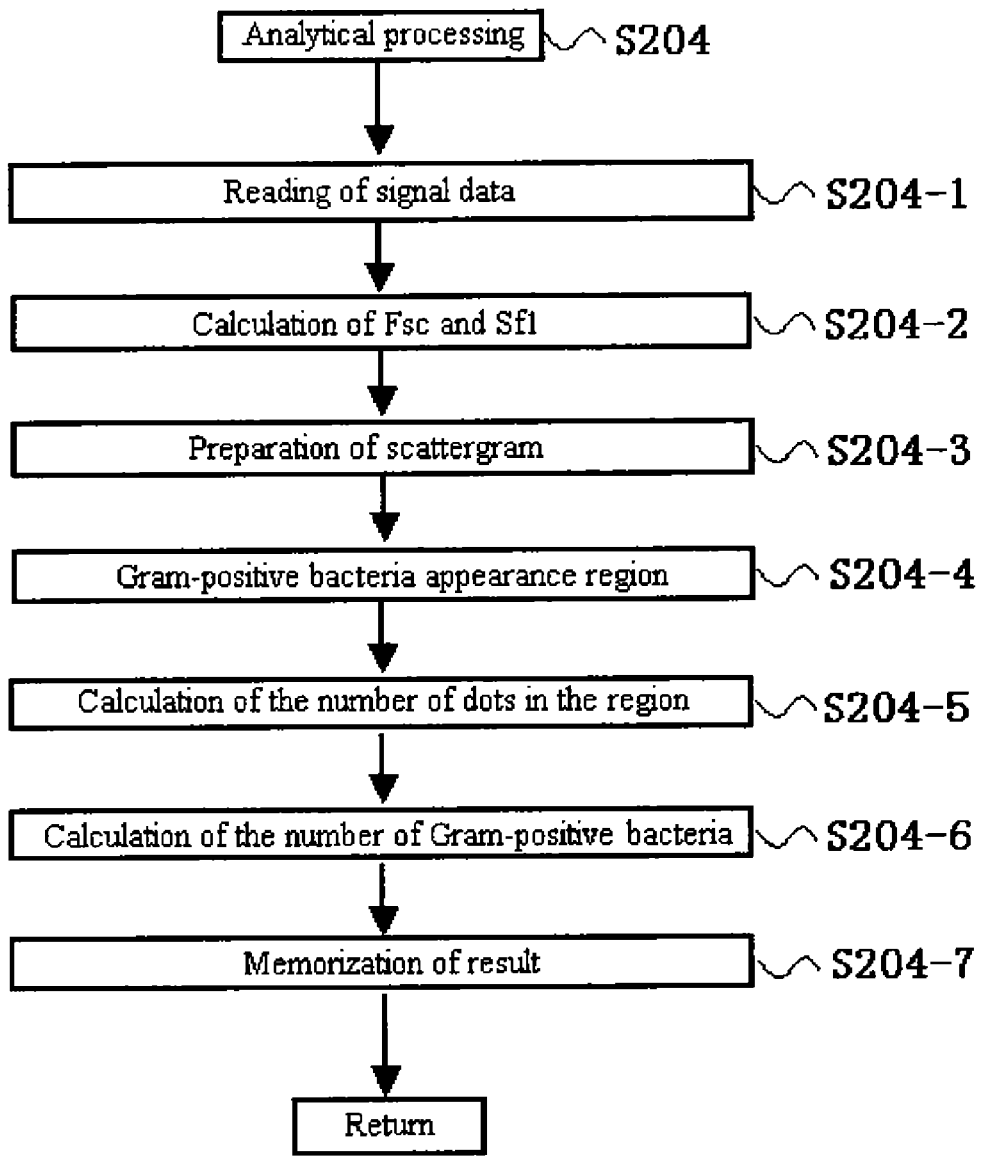
FIG. 10 shows the flow of analysis in measurement B in one embodiment of the present invention.

When the forward scattered light signal and side fluorescence signal are detected by measurement processing in S203, the analysis section 38 analyzes each signal on the basis of an analysis program. The operation of the analysis program in analytical processing is described by reference to the flow chart in FIG. 10. Each step in the flow chart is as follows:

S204-1: Data on the forward scattered light signal and side fluorescence signal detected in the sample are read from the memory section 37. The procedure is followed by S204-2.

S204-2: On the basis of the forward scattered light signal and side fluorescence signal obtained from each particle in the analytic sample, the forward scattered light intensity (Fsc) and side fluorescence intensity (FL) are calculated. The procedure is followed by S204-3.

S204-3: Fsc and FL for each particle calculated in S204-2 are used as parameters to prepare a scattergram. First, two-dimensional coordinates with Fsc and FL coordinate axes are developed, and on the basis of Fsc and FL, a coordinate position corresponding to each particle in the analytic sample is determined. The scattergram with Fsc and FL as parameters is thus prepared. The procedure is followed by S204-4.

Figure 12B:
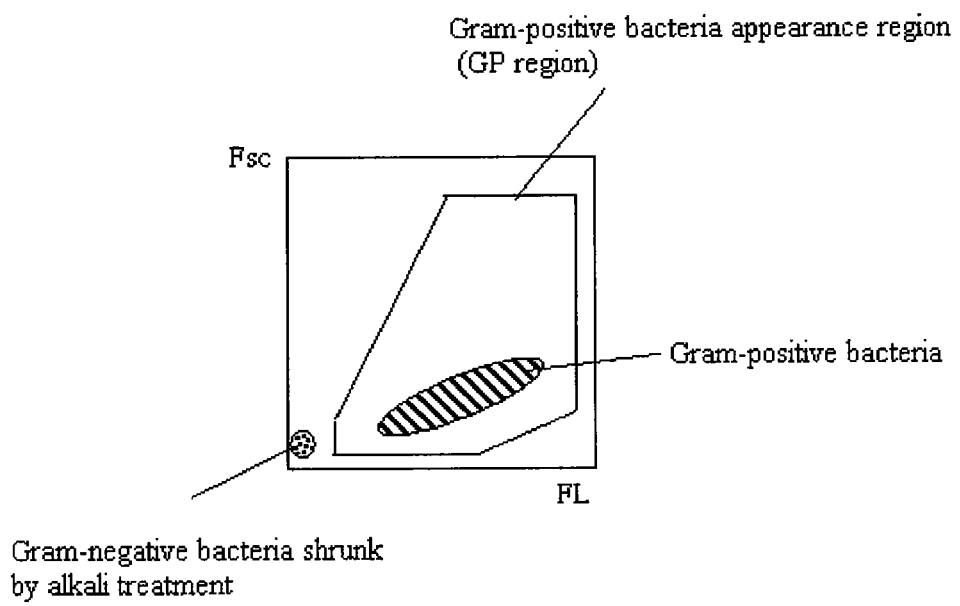

S204-4: On the prepared scattergram, a region where Gram-positive bacteria appear (this region is referred to as GP region) is established. The GP region is established on the scattergram, as shown in FIG. 12B. The GP region thus established is empirically determined by previously measuring an analytic sample prepared by adding an alkaline solution to a specimen containing bacteria confirmed to be Gram-positive bacteria or Gram-negative bacteria. Dots corresponding to Gram-positive bacteria contained in the sample appear in the GP region. The GP region is memorized in the memory section 37, read by the analysis program in S204-4, and applied to the scattergram. The procedure is followed by S204-5.

S204-5: The number of dots in the GP region is counted. This is followed by S204-6.

S204-6: On the basis of the number of dots counted in S204-5, the number of Gram-positive bacteria contained in the specimen is calculated. On the scattergram, dots corresponding to Gram-positive bacteria appear on the GP region. On the basis of the number of dots appearing on the GP region, the number of Gram-positive bacteria contained in the specimen can be calculated. In this example, the number of Gram-positive bacteria contained per μL of the specimen is calculated from the determined number of dots. This is followed by S204-7.

S204-7: Data on the number of dots in the GP region calculated in S204-5 and data on the number of Gram-positive bacteria calculated in S204-6 are memorized.

As described above, FIG. 12B is shown to explain the scattergram prepared in S204-3 and S204-4. In the scattergram, FL is shown on the abscissa, and Fsc on the ordinate. The value of FL is increased in the direction from left to right on the abscissa. The value of Fsc is increased in the upward direction on the ordinate. Gram-positive bacteria contained in the analytic sample appear on the GP region established on the scattergram. On the other hand, Gram-negative bacteria contained in the analytic sample are damaged and shrunk by alkali treatment. Therefore, the forward scattered light intensity and florescence intensity obtained from the Gram-negative bacteria are smaller than those from Gram-positive bacteria, and thus the Gram-negative bacteria appear in the vicinity of the origin of the coordinate axes on the scattergram. Accordingly, the Gram-negative bacteria and Gram-positive bacteria can be easily distinguished from each other by differences in the forward scattered light intensity and fluorescence intensity.

S3 (Comprehensive Analysis)

Figure 11:
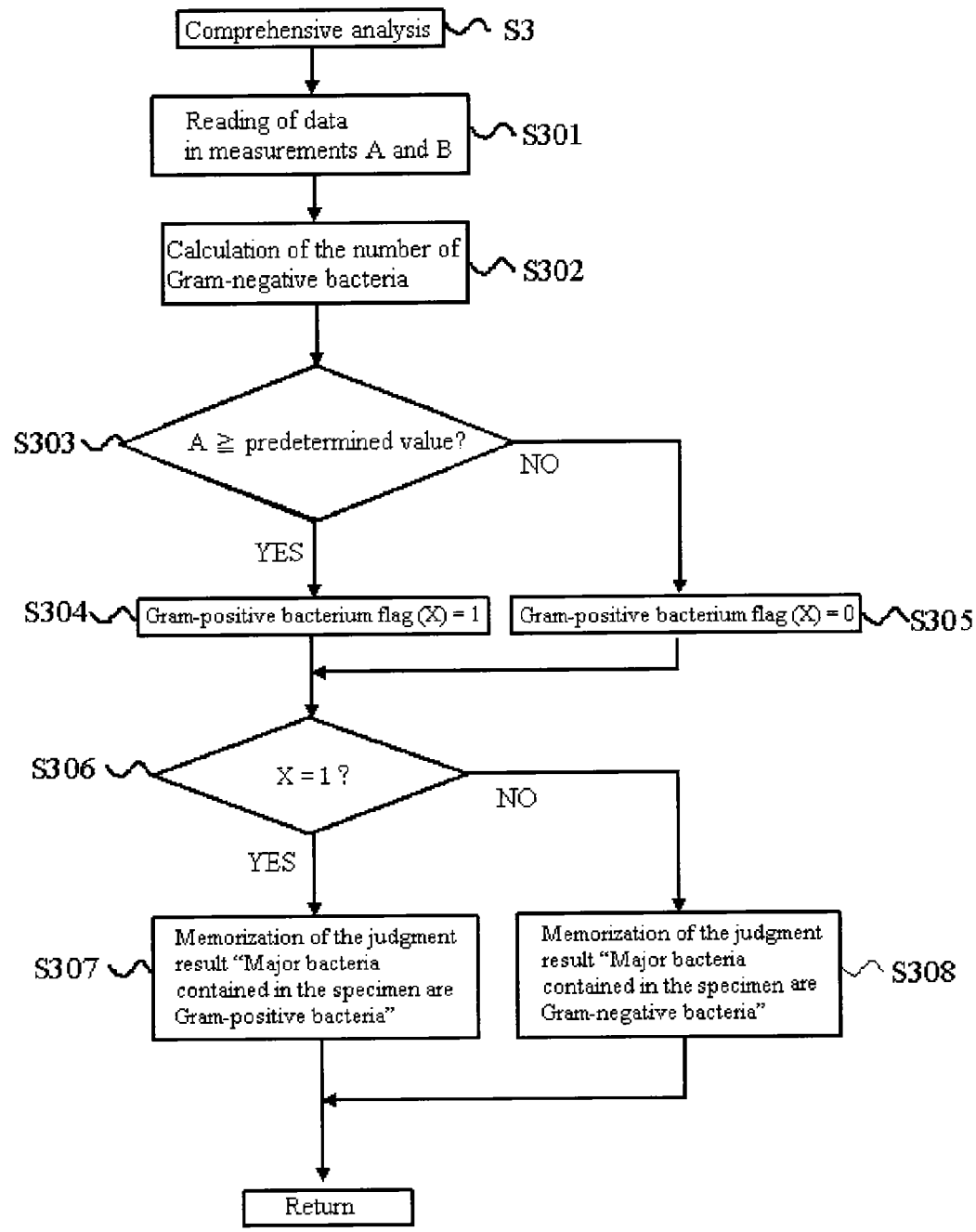
FIG. 11 shows the flow of comprehensive analysis in one embodiment of the present invention.

The data obtained in measurements A and B are analyzed on the basis of the analysis program. The operations of the analysis program in this comprehensive analysis are described by reference to the flow chart in FIG. 11. Each step in the flow chart is as follows.

S301: Data on the number of total bacteria obtained in measurement A and data on the number of Gram-positive bacteria obtained in measurement B are read. This is followed by step S302.

S302: On the basis of each data, the number of Gram-negative bacteria is calculated by subtracting the number of Gram-positive bacteria from the number of the total bacteria. In measurement B, the Gram-negative bacteria are shrunk by alkali treatment. Accordingly, the Gram-negative bacteria appear intensively in the vicinity of the origin of the coordinate axes on the scattergram obtained in measurement B. However, when contaminants are contained in the specimen, there are cases where the contaminants appear in the vicinity of the origin of the coordinate axes on the scattergram. This is because the scattered light intensity and fluorescence intensity of the contaminants are also very low. Accordingly, the number of Gram-negative bacteria can be easily determined by subtracting the number of Gram-positive bacteria determined in measurement B from the number of the total bacteria determined in measurement A. The procedure is followed by S303.

S303: The number of Gram-positive bacteria is compared in the following manner with the number of Gram-negative bacteria calculated in step S302. First, A is determined from the following equation:

$$GP/(GP+GN)=A$$

wherein GP is the number of Gram-positive bacteria, and GN is the number of Gram-negative bacteria.

When the value of A calculated from the above equation is equal or higher than a predetermined value, the procedure is followed by S304. On the other hand, when the value of A is less than a predetermined value, the procedure is followed by step S305.

S304: Gram-positive bacterium flag X is set at "1". This step is followed by S306.

S305: Gram-positive bacterium flag X is set at "0". This step is followed by S306.

S306: The procedure of judging whether the Gram-positive bacterium flag X is "1" or not is executed in S306. When the Gram-positive bacterium flag X is "1", the procedure is followed by S307, while when the Gram-positive bacterium flag X is "0", the procedure is followed by S308.

S307: The result "Major bacteria contained in the specimen are Gram-positive bacteria" is memorized.

S308: The result "Major bacteria contained in the specimen are Gram-negative bacteria" is memorized.

S4 (Output)

In output in S4, the following result is output and displayed on the liquid crystalline touch panel 2.

The scattergram and the number of total bacteria obtained in S1 (measurement A).

The scattergram and the number of Gram-positive bacteria obtained in S2 (measurement B).

The number of Gram-negative bacteria and the judgment result "Major bacteria contained in the specimen are Gram-positive bacteria" or "Major bacteria contained in the specimen are Gram-negative bacteria" obtained in S3 (comprehensive analysis).

The foregoing is a flow chart of the measurement in this example.

Measurement Example 1

Using the bacteria analyzing apparatus 1 described above, a specimen was analyzed as follows. The specimen used was a culture obtained by culturing objective bacteria to a density of about $10^5$ cells/ml in a heart infusion liquid medium. In this example, cultures of the following 6 kinds of bacteria were prepared and used as specimens. In the 6 kinds of bacteria, Gram-negative bacteria are the following 3 bacteria:

Acinetobacter baumannii (ATCC 19606) (hereinafter, referred to as "A. baumannii")
Escherichia coli (ATCC 25922) (hereinafter, referred to as "E. coli")
Klebsiella pneumoniae (ATCC 700603) (hereinafter, referred to as "K. pneumoniae")

Gram-positive bacteria are the following 3 bacteria:

Enterococcus faecalis (ATCC 29212) (hereinafter, referred to as "E. faecalis")
Staphylococcus aureus (ATCC 29213) (hereinafter, referred to as "S. aureus")
Lactobacilllus achidophilus (ATCC 4356) (hereinafter, referred to as "L. achidophilus").

In this example, a culture of A. baumannii is referred to as specimen (I), a culture of E. coli as specimen (II), a culture of K. pneumoniae as specimen (III), a culture of E. faecalis as specimen (IV), a culture of S. aureus as specimen (V), and a culture of L. achidophilus as specimen (VI).

Scattergrams obtained by analyzing the specimens (I) to (VI) by using the bacteria analyzing apparatus 1 are shown in FIGS. 13, 14, 15, 16, 17 and 18, respectively.

Figure 13A:
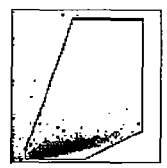
FIGS. 13A and 13B show one example of a two-dimensional scattergram prepared by the bacteria analyzing apparatus in one embodiment of the present invention.
Figure 13B:
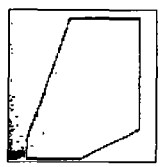

FIG. 13 is a scattergram obtained by analyzing the specimen (I). FIG. 13A is a scattergram obtained by measurement A (without alkali treatment), and FIG. 13B is a scattergram obtained by measurement B (with alkali treatment).

Figure 14A:
FIGS. 14A and 14B show one example of a two-dimensional scattergram prepared by the bacteria analyzing apparatus in one embodiment of the present invention.
Figure 14B:
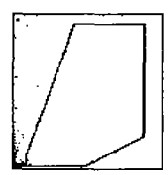

FIG. 14 is a scattergram obtained by analyzing the specimen (II). FIG. 14A is a scattergram obtained by measurement A (without alkali treatment), and FIG. 14B is a scattergram obtained by measurement B (with alkali treatment).

Figure 15A:
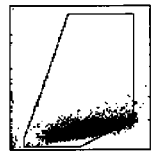
FIGS. 15A and 15B show one example of a two-dimensional scattergram prepared by the bacteria analyzing apparatus in one embodiment of the present invention.
Figure 15B:
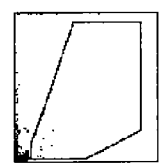

FIG. 15 is a scattergram obtained by analyzing the specimen (III). FIG. 15A is a scattergram obtained by measurement A (without alkali treatment), and FIG. 15B is a scattergram obtained by measurement B (with alkali treatment).

In FIGS. 13A, 14A and 15A which are scattergrams obtained by measurement A, dots corresponding to the Gram-negative bacteria appear in the GPN region where total bacteria appear. On the other hand, FIGS. 13B, 14B and 15B which are scattergrams obtained by measurement B, none of dots appear in the GP region where Gram-positive bacteria appear, and dots appear in the vicinity of the origin.

Figure 16A:
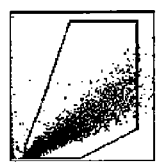
FIGS. 16A and 16B show one example of a two-dimensional scattergram prepared by the bacteria analyzing apparatus in one embodiment of the present invention.
Figure 16B:
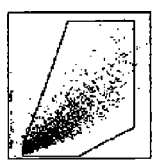

FIG. 16 is a scattergram obtained by analyzing the specimen (IV). FIG. 16A is a scattergram obtained by measurement A (without alkali treatment), and FIG. 16B is a scattergram obtained by measurement B (with alkali treatment).

Figure 17A:
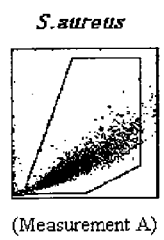
FIGS. 17A and 17B show one example of a two-dimensional scattergram prepared by the bacteria analyzing apparatus in one embodiment of the present invention.
Figure 17B:

FIG. 17 is a scattergram obtained by analyzing the specimen (V). FIG. 17A is a scattergram obtained by measurement A (without alkali treatment), and FIG. 17B is a scattergram obtained by measurement B (with alkali treatment).

Figure 18A:
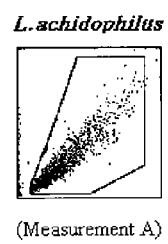
FIGS. 18A and 18B show one example of a two-dimensional scattergram prepared by the bacteria analyzing apparatus in one embodiment of the present invention.
Figure 18B:
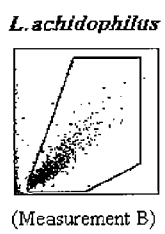

FIG. 18 is a scattergram obtained by analyzing the specimen (VI). FIG. 18A is a scattergram obtained by measurement A (without alkali treatment), and FIG. 18B is a scattergram obtained by measurement B (with alkali treatment).

In FIGS. 16A, 17A and 18A which are scattergrams obtained by measurement A, dots corresponding to the Gram-positive bacteria appear in the GPN region where total bacteria appear. On the other hand, FIGS. 16B, 17B and 18B which are scattergrams obtained by measurement B, dots appear in the GP region where Gram-positive bacteria appear.

From FIGS. 13, 14, 15, 16, 17 and 18, it could be confirmed that in measurement A, both the Gram-negative bacteria and Gram-positive bacteria appear in the GPN region. It could also be confirmed that in measurement B, the Gram-negative bacteria appears outside of the GP region, while the Gram-positive bacteria appear in the GP region. The Gram-negative bacteria and Gram-positive bacteria are significantly different from each other in respect of the position where their dots appear, and thus the Gram-negative bacteria and Gram-positive bacteria can be easily distinguished from each other.

Then, whether major bacteria contained in each of the specimens (I) to (VI) are Gram-positive or Gram-negative bacteria was judged by the bacteria analyzing apparatus 1. The results are collectively shown in the following table.

TABLE 1

| Specimen | Judgment result |
| --- | --- |
| I | Gram-negative bacteria |
| II | Gram-negative bacteria |
| III | Gram-negative bacteria |
| IV | Gram-positive bacteria |
| V | Gram-positive bacteria |
| VI | Gram-positive bacteria |

As shown in Table 1, the major bacteria contained in the specimens (I), (II) and (III) were judged to be Gram-negative bacteria, and the major bacteria contained in the specimens (IV), (V) and (VI) were judged to be Gram-positive bacteria. The judgment results by this analysis reveal that in any specimens (I) to (VI), the judged bacterial species agree with the bacterial species contained actually in each specimen.

In the bacteria analyzing apparatus 1 in this example, the morphological difference is caused between Gram-negative bacteria and Gram-positive bacteria, whereby the Gram-negative bacteria and Gram-positive bacteria can be easily distinguished from each other by using a single dye in place of a plurality of dyes. Accordingly, Gram-negative bacteria and Gram-positive bacteria can be detected easily and rapidly. In the example described above, the Gram-negative bacteria and Gram-positive bacteria contained in the specimens can be rapidly detected, and whether the major bacteria contained in the specimen are Gram-negative bacteria or Gram-positive bacteria can be judged.

Figure 19:
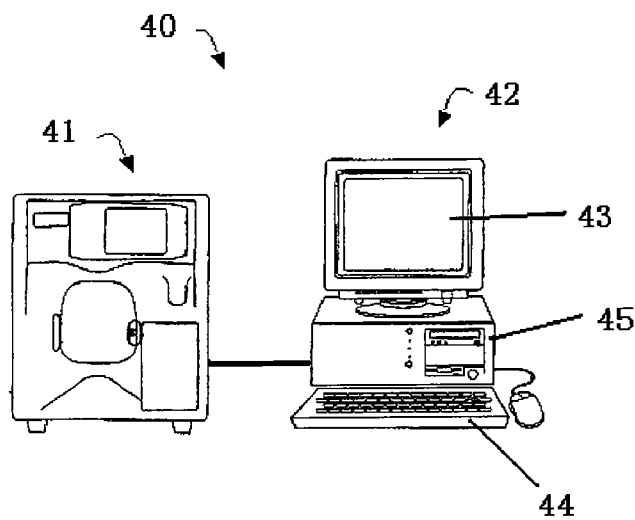
FIG. 19 shows the constitution of the bacteria analyzing apparatus in another embodiment of the present invention.

The bacteria analyzing apparatus 1 in the example described above is a apparatus in which every constitution is embodied, but the present invention is not limited to such constitution. For example, the bacteria analyzing apparatus may be a apparatus from which a partial constitution is separated as shown in FIG. 19. The bacteria analyzing apparatus 40 in FIG. 19 is comprised of a measuring main body 41 and a personal computer 42. Although not shown in the figure, the measuring main body 41 has a start switch, an analytic sample preparation section for preparing an analytic sample, a measurement section for detecting signals from the analytic sample, and a first control section for controlling the operations of the apparatus. The first control section includes a first memory section for memorizing a control program for regulating the operations of each apparatus and an operation control section for regulating the operations of each apparatus on the basis of the control program memorized in the first memory section. The personal computer 42 includes an output display 43 for displaying measurement results, an input section 44 for inputting the setting and a second control section 45 for controlling analytical processing. The second control section 45 includes a second memory section for memorizing an analysis program and processing results by the analysis program and an analysis section for executing analysis on the basis of data obtained by measurement. In FIG. 19, the measuring main body 41 is connected via a connector to the personal computer 42. The operations of each section in the apparatus are regulated by the first control section in the measuring main body 41. Measurement data obtained by the measuring main body 41 are memorized in the second memory section in the personal computer 42 and analyzed in the analysis section.

In the example described above, the bacteria are cultured in a medium solution, and the resulting culture is used as a specimen. In the present invention, however, not only the microbial culture but also a clinical sample such as urine and blood collected from a patient can be subjected to measurement as it is. The Gram stainability classification of bacteria contained in the specimen can thereby be rapidly effected.

Whether the major bacteria contained in a specimen are Gram-negative bacteria or Gram-positive bacteria is judged in S3 (comprehensive analysis) in the bacteria analyzing apparatus 1 in the example described above, but the present invention is not limited thereto. For example, when "a specimen containing one kind of bacteria" such as used in Measurement Example 1 is to be analyzed, it is evident that one kind of bacteria is contained in the specimen, and thus the bacteria in the specimen can be classified into either Gram-negative or Gram-positive bacteria. In this case, therefore, whether the kind of the bacteria contained in the specimen is Gram-negative bacteria or Gram-positive bacteria may be judged in S3 (comprehensive analysis).

In the bacteria analyzing apparatus 1 in the example described above, measurement A wherein an analytic sample is prepared without subjecting a specimen to alkali treatment and measurement B wherein an analytic sample is prepared by subjecting a specimen to alkali treatment are carried out, and the number of Gram-negative bacteria is calculated by subtracting the number of Gram-positive bacteria obtained in measurement B from the number of total bacteria obtained in measurement A, but the present invention is not limited thereto. For example, only measurement B wherein an analytic sample is prepared by subjecting a specimen to alkali treatment may be conducted. In this case, the number of Gram-positive bacteria contained in the specimen can be calculated based on dots corresponding to Gram-positive bacteria in the GP region established in the scattergram.

Figure 20:
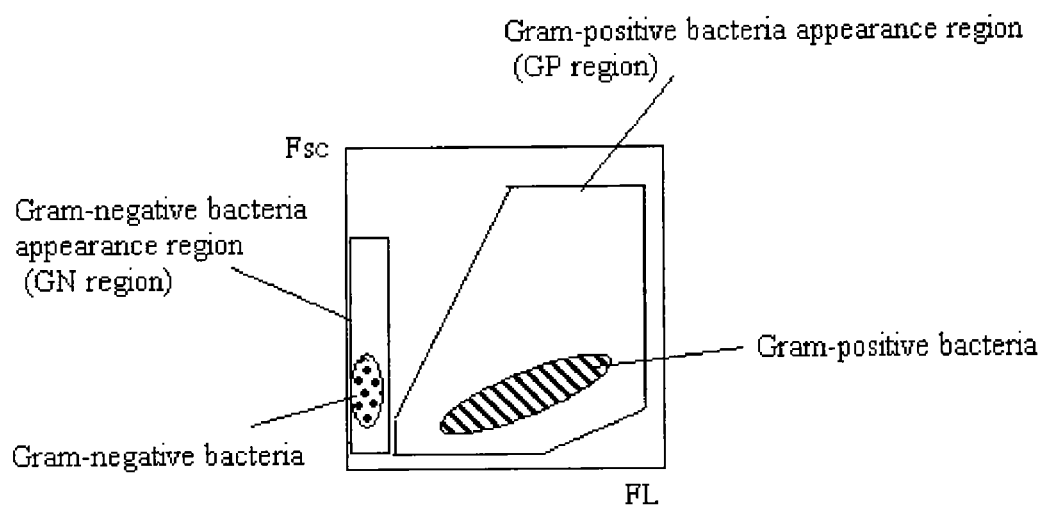
FIG. 20 shows one example of a two-dimensional scattergram prepared by the bacteria analyzing apparatus in another embodiment of the present invention.

In the bacteria analyzing apparatus 1 in the example described above, the number of Gram-negative bacteria is calculated by subtracting the number of Gram-positive bacteria from the number of total bacteria, but the present invention is not limited thereto. After Gram-negative bacteria are detected, the number of the detected Gram-negative bacteria may be calculated. As shown in FIG. 20, for example, the region (GN region) where Gram-negative bacteria appear is established, and on the basis of dots corresponding to Gram-negative bacteria appearing in the GN region, the number of the Gram-negative bacteria contained in the specimen may be calculated. Further, the number of the Gram-positive bacteria may be calculated by subtracting the number of the Gram-negative bacteria from the number of total bacteria.

In this example, the morphological difference is caused between Gram-negative bacteria and Gram-positive bacteria, whereby the Gram-positive bacteria contained in the specimen can be easily and rapidly detected. In this example, the Gram-negative bacteria and Gram-positive bacteria can be easily and rapidly detected.

What is claimed is:

1. An apparatus for discriminately analyzing a first type of constituents and a second type of constituents contained in a sample, the apparatus comprising a processor of a computer system and a memory with a storage medium that stores programs executable by the processor, wherein the programs are operative to:

flow a quantity of the sample through a flow cytometer and detect first and second signals from the flow cytometer which are indicative respectively of first and second optical characteristics of the constituents;

scale the detected first and second signals onto a two-dimensional scale, wherein the first and second optical characteristics are scalable respectively along two axes of the two-dimensional scale;

read from the memory a first two-dimensional threshold defined to delineate, on the two-dimensional scale, a first region within which both the first and second types of constituents are empirically determined likely to exhibit their first and second optical characteristics;

apply the first two-dimensional threshold to the first and second signals scaled onto the two-dimensional scale to derive a first count indicative of a number of the first and second types of constituents countable within the first region on the two-dimensional scale;

flow another quantity of the sample through the flow cytometer, which is treated with a chemical that can cause different degrees of change to at least one of the first and second optical characteristics between the first and second types of constituents, and detect third and fourth signals from the flow cytometer which are indicative respectively of the first and second optical characteristics of the chemically treated constituents;

scale the detected third and fourth signals onto the two-dimensional scale;

read from the memory a second two-dimensional threshold defined to delineate, on the two-dimensional scale, a second region inside which the chemically treated first type of constituents are empirically determined likely to exhibit their first and second optical characteristics and outside which the chemically treated second type of constituents are empirically determined likely to exhibit their first and second optical characteristics;

apply the second two-dimensional threshold to the third and fourth signals scaled onto the two-dimensional scale to derive a second count indicative of a number of the chemically treated first type of constituents countable within the second region on the two-dimensional scale; and calculate a ratio of the second count to the first count to present a criterion for determining whether the sample contains the first type of constituents or the second type of constituents.

2. The apparatus according to claim 1, wherein the first type of constituents are Gram-positive bacteria and the second type of constituents are Gram-negative bacteria.

3. The apparatus according to claim 1, wherein the chemical is an alkaline solution, which causes one of the first and second types of constituents to become smaller than the other.

4. The apparatus according to claim 1, wherein the first and second signals are from forward scattered light and side fluorescence light of the flow cytometer.

5. The apparatus according to claim 1, wherein the programs further comprise a program executable by the processor to subtract the first count with the second count to derive a third count, which is indicative of a number of the second type of constituents countable within the first region on the two-dimensional scale.

6. A method for discriminately analyzing a first type of constituents and a second type of constituents contained in a sample, the method comprises computer-executable steps performed by a processor of a computer system to implement:
  flowing a quantity of the sample through a flow cytometer and detecting first and second signals from the flow cytometer which are indicative respectively of first and second optical characteristics of the constituents;
  scaling the detected first and second signals onto a two-dimensional scale, wherein the first and second optical characteristics are scalable respectively along two axes of the two-dimensional scale;
  reading from the memory a first two-dimensional threshold defined to delineate, on the two-dimensional scale, a first region within which both the first and second types of constituents are empirically determined likely to exhibit their first and second optical characteristics;
  applying the first two-dimensional threshold to the first and second signals scaled onto the two-dimensional scale to derive a first count indicative of a number of the first and second types of constituents countable within the first region on the two-dimensional scale;
  flowing through the flow cytometer another quantity of the sample, which is treated with a chemical that can cause different degrees of change to at least one of the first and second optical characteristics between the first and second types of constituents, and detecting third and fourth signals from the flow cytometer which are indicative respectively of the first and second optical characteristics of the chemically treated constituents;
  scaling the detected third and fourth signals onto the two-dimensional scale;
  read from the memory a second two-dimensional threshold defined to delineate, on the two-dimensional scale, a second region inside which the chemically treated first type of constituents are empirically determined likely to exhibit their first and second optical characteristics and outside which the chemically treated second type of constituents are empirically determined likely to exhibit their first and second optical characteristics;
  applying the second two-dimensional threshold to the third and fourth signals scaled onto the two-dimensional scale to derive a second count indicative of a number of the chemically treated first type of constituents countable within the second region on the two-dimensional scale; and
  calculating a ratio of the second count to the first count to present a criterion for determining whether the specimen contains the first type of constituents or the second type of constituents.

7. The method according to claim 6, wherein the first type of constituents are Gram-positive bacteria and the second type of constituents are Gram-negative bacteria.

8. The method according to claim 6, wherein the chemical is an alkaline solution, which causes one of the first and second types of constituents to become smaller than the other.

9. The method according to claim 6, wherein the first and second signals are from forward scattered light and side fluorescence light of the flow cytometer.

10. The method according to claim 6, wherein further comprising subtracting the first count with the second count to derive a third, which is indicative of a number of the second type of constituents countable within the first region on the two-dimensional scale.

11. A non-transitory storage medium which stores programs executable by a processor of an apparatus for discriminately analyzing a first type of constituents and a second type of constituents contained in a sample, the program being executable by the processor to:
  flow a quantity of the sample through a flow cytometer and detect first and second signals from the flow cytometer which are indicative respectively of first and second optical characteristics of the constituents;
  scale the detected first and second signals onto a two-dimensional scale, wherein the first and second optical characteristics are scalable respectively along two axes of the two-dimensional scale;
  read from the memory a first two-dimensional threshold defined to delineate, on the two-dimensional scale, a first region within which both the first and second types of constituents are empirically determined likely to exhibit their first and second optical characteristics;
  apply the first two-dimensional threshold to the first and second signals scaled onto the two-dimensional scale to derive a first count indicative of a number of the first and second types of constituents countable within the first region on the two-dimensional scale;
  flow through the flow cytometer another quantity of the sample, which is treated with a chemical that can cause different degrees of change to at least one of the first and second optical characteristics between the first and second types of constituents, and detecting third and fourth signals from the flow cytometer which are indicative respectively of the first and second optical characteristics of the chemically treated constituents;
  scale the detected third and fourth signals onto the two-dimensional scale;
  read from the memory a second two-dimensional threshold defined to delineate, on the two-dimensional scale, a second region inside which the chemically treated first type of constituents are empirically determined likely to exhibit their first and second optical characteristics and outside which the chemically treated second type of constituents are empirically determined likely to exhibit their first and second optical characteristics;
  apply the second two-dimensional threshold to the third and fourth signals scaled onto the two-dimensional scale to derive a second count indicative of a number of the chemically treated first type of constituents countable within the second region on the two-dimensional scale; and
  calculate a ratio of the second count to the first count to present a criterion for determining whether the specimen contains the first type of constituents or the second type of constituents.

12. The storage medium according to claim 11, wherein the first type of constituents are Gram-positive bacteria and the second type of constituents are Gram-negative bacteria.

13. The storage medium according to claim 11, wherein the chemical is an alkaline solution, which causes one of the first and second types of constituents to become smaller than the other.

14. The storage medium according to claim 11, wherein the first and second signals are from forward scattered light and side fluorescence light of the flow cytometer.

15. The storage medium according to claim 11, wherein the programs further comprise a program executable by the processor to subtract the first count with the second count to derive a third count, which is indicative of a number of the second type of constituents countable within the first region on the two-dimensional scale.

* * * * *